United States Patent
Keller

(10) Patent No.: US 7,048,742 B2
(45) Date of Patent: May 23, 2006

(54) INSERTION INSTRUMENT FOR SLIDING PROSTHESES

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 416 days.

(21) Appl. No.: 10/287,686

(22) Filed: Nov. 5, 2002

(65) Prior Publication Data
US 2003/0109929 A1 Jun. 12, 2003

(30) Foreign Application Priority Data
Dec. 10, 2001 (EP) ............................. 01129441

(51) Int. Cl.
*A61F 2/38* (2006.01)

(52) U.S. Cl. ........................................... 606/88

(58) Field of Classification Search .......... 606/82, 606/88, 89, 99, 205; 623/20.14, 20.15, 20.31
See application file for complete search history.

(56) References Cited

U.S. PATENT DOCUMENTS

| 3,949,428 A | | 4/1976 | Cavendish et al. |
| 5,395,370 A | * | 3/1995 | Muller et al. ................. 606/61 |
| 6,743,258 B1 | * | 6/2004 | Keller ..................... 623/20.14 |

FOREIGN PATENT DOCUMENTS

EP   1 099 430 A1   5/2001

* cited by examiner

*Primary Examiner*—Pedro Philogene
*Assistant Examiner*—D. Jacob Davis
(74) *Attorney, Agent, or Firm*—Morrison & Foerster LLP

(57) ABSTRACT

An instrument for inserting a pair of sliding prostheses includes a supporting plate, two clamps adjustable through a spacing range, and two vertically adjustable sliding-surface bearing supports configured to support the sliding prostheses in the area of the sliding surfaces on the supports. Each of the clamps is configured to receive one of the pair of sliding prostheses and has clamping jaws configured to interact with the side edges of the corresponding sliding prostheses. The supporting plate has a slide guide formed thereon and an adjustment spindle for at least one of the two clamps. The sliding-surface bearing supports are configured in fixed positions on the supporting plate and having a width which corresponds to the adjustable spacing range of the clamps and is large enough to support the sliding prostheses in any chosen spacing.

8 Claims, 3 Drawing Sheets

INSERTION INSTRUMENT FOR SLIDING PROSTHESES

FIELD AND BACKGROUND OF THE INVENTION

The human knee-joint comprises two pairs of tibio-femoral articular surfaces, namely a medial pair of articular surfaces and a lateral pair of articular surfaces, which are in each case formed by a femoral condyle and, respectively, by a dish-shaped tibial or meniscal articular surface interacting with said femoral condyle. In prosthetic simulation of this joint, the femoral slide surfaces are formed either by a one-piece prosthesis part or by two separate prosthesis parts. The latter are referred to as sliding prostheses. To ensure that the femoral and tibial articular slide surfaces can interact correctly, their lateral spacing must be identical. When using sliding prostheses, this means that their spacing must be exactly maintained. For this purpose, insertion instruments are known (EP-A-1 099 430) in which two clamps are arranged on a supporting plate of the instrument and are each intended to receive a sliding prosthesis. The spacing between these clamps can be adjusted according to the requirements of the associated tibial prosthesis part. The clamping jaws of the clamps each interact with the side edges of the sliding prostheses. Since force transmission is limited at this position, a vertically adjustable slide-surface support is also provided in each clamp and takes up a large part of the force transmitted from the instrument to the prosthesis parts during implantation.

In the known instrument, one clamping jaw of each of the clamps is connected to the supporting plate in a nonadjustable manner and it supports the laterally adjustable second clamping jaw. If one wants to change the spacing between the clamps, another supporting plate or other clamps are chosen. A supply of different supporting plates or clamps must therefore be kept. This is expensive. It is also difficult, during the operation, to choose a clamp spacing different than the one selected during the preparations for the operation. The arrangement of the slide-surface supports on the clamps is disadvantageous because their arrangement is complicated and access to them difficult.

In another known insertion instrument for sliding prostheses (U.S. Pat. No. 3,949,428), the clamps themselves are not adjustable. Instead, the clamping jaws have guide tracks which interact with corresponding grooves in the sliding prostheses. To ensure that they can be released again from the sliding prostheses after the latter have been implanted, the grooves on the sliding prostheses must be open at the end. Since they cannot open into the slide surfaces themselves, this solution cannot be employed in the sliding prostheses customary today. The spacing of the clamps from one another can be adjusted because they are arranged displaceably on a holding frame and each have a locking screw by means of which their respective chosen position can be fixed. This is a very elaborate arrangement which scarcely permits the spacing to be changed under the conditions existing during surgery.

SUMMARY OF THE INVENTION

Starting from the prior art set out above, a feature of the invention is to simplify the construction and make it easier to use. This is achieved by means of the invention as disclosed in this application.

Accordingly, the instrument according to the invention is characterized by the fact that the supporting plate has a slide guide with adjustment spindle for at least one of the two clamps, and the slide-surface supports are also arranged in a fixed position on the supporting plate and have a width which corresponds to the adjustment range. By actuating the adjustment spindle, the spacing of the clamps can be easily adjusted. This feature also makes it easier to detach the instrument from the implanted prostheses. Not only are the clamps widened for this purpose, it is also possible, by means of the adjustment of the spacing, for those clamping jaws which remain unchanged during widening of the clamps to be disengaged from the prosthesis parts. As regards the arrangement of the slide-surface supports, the invention has recognized that these do not necessarily have to be arranged exactly where the sliding prostheses are located. This would mean that their spacing would have to be changed together with that of the clamps. For this reason, the slide-surface supports in the known instrument mentioned in the introduction were located on the clamps themselves. The invention has recognized that the construction can be considerably simplified if the slide-surface supports are arranged with constant spacing on the supporting plate. In this case, it is simply necessary for them to be wide enough to be able to interact sufficiently with the prosthesis parts in any chosen spacing of the latter. The arrangement of the slide-surface supports separate from the clamps has the consequence that the prosthesis fixtures located in the clamps are arranged offset in the anterior-posterior direction relative to the slide-surface supports. This is advantageous because in this way the prosthesis parts can be more securely gripped by the instrument and considerable forces can be transmitted to the prostheses without any fear of their position changing.

In order to be able to adjust the spacing of the clamps from one another, it is sufficient if the supporting plate has only one slide guide with adjustment spindle for one of the two clamps. However, depending on the spacing chosen, this can result in an asymmetrical arrangement of the clamps. It is therefore more expedient if both clamps are held in slide guides of the supporting plate and the adjustment spindle acts on both clamps in the opposite direction.

The clamps expediently consist of a clamping jaw connected directly to the supporting plate, and of a clamping jaw which is held by the latter clamping jaw and is adjustable relative thereto. However, this does not rule out the case in which each clamping jaw consists of a base part held by the supporting plate and of two clamping jaws adjustable relative to the base part.

According to an important feature of the invention, the slide-surface supports are assigned to the slide-surface portion extending in the anterior-posterior direction, because the sliding prostheses are generally applied to the femur in a distally extending direction and the slide-surface supports can therefore take up most of the application force. Anchoring pins which may be present on the proximal side of the prostheses also generally extend in this direction. However, if the anchoring pins were to extend in another direction, it may be more expedient to arrange the slide-surface supports in such a way that they act in this other direction.

The slide-surface supports should be vertically adjustable so that they can be adapted to different prosthesis shapes.

BRIEF DESCRIPTION OF THE DRAWINGS

The invention is explained in greater detail below with reference to the drawings which depict an advantageous illustrative embodiment and in which.

DETAILED DESCRIPTION OF THE INVENTION

Figure 2:
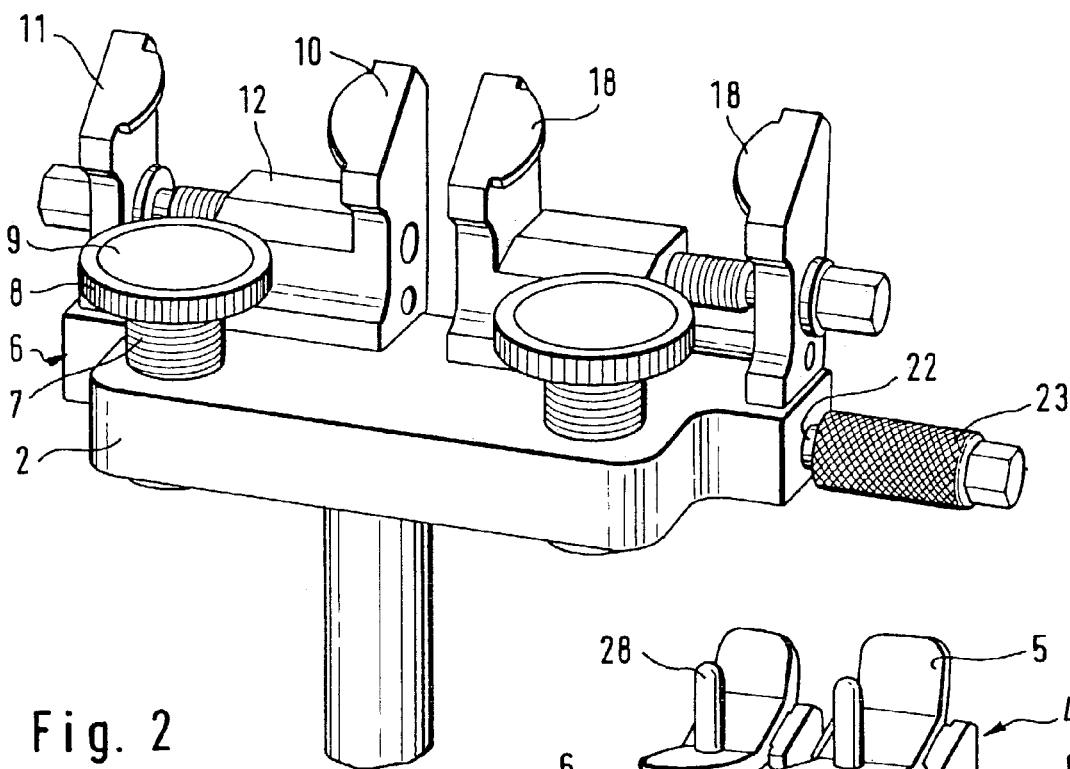
FIG. 2 shows the front part of the instrument on a larger scale, without the sliding prostheses.
Figure 1:
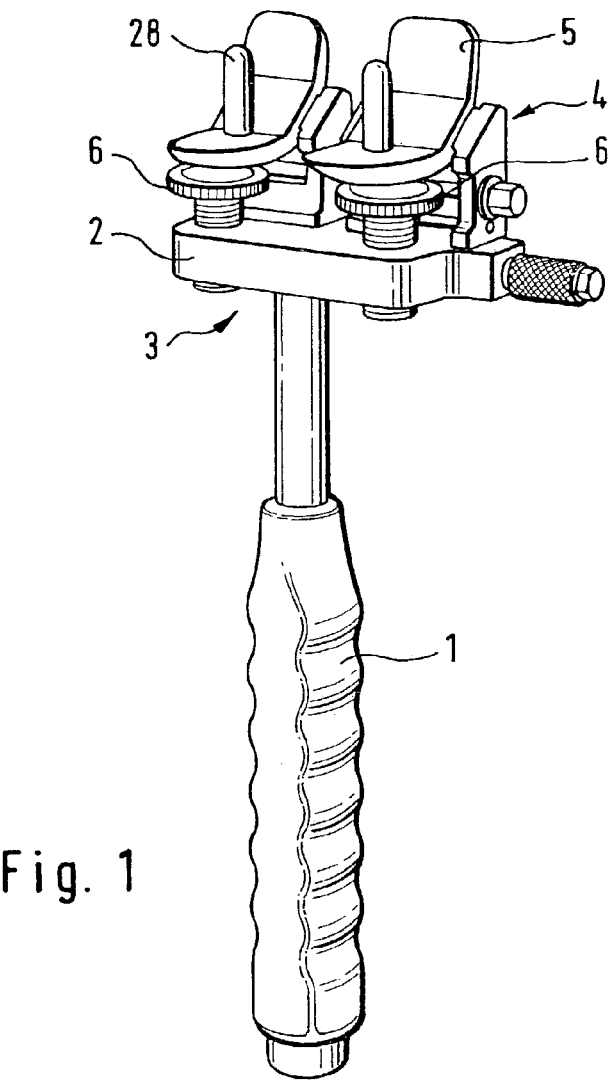
FIG. 1 shows an overall view of the instrument with attached sliding prostheses.
Figure 3:
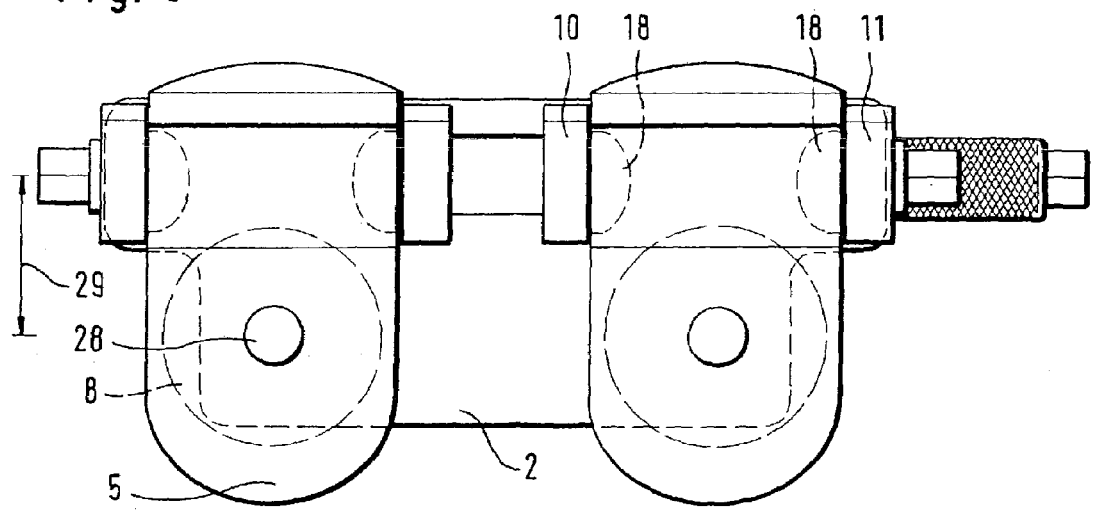
FIG. 3 shows a head-on view of the instrument with attached sliding prostheses.

The supporting plate 2 of the front instrument part 3 is secured on a handle with grip 1. The supporting plate supports two clamps 4 for two sliding prostheses 5, and two slide-surface supports 6.

Figure 4:
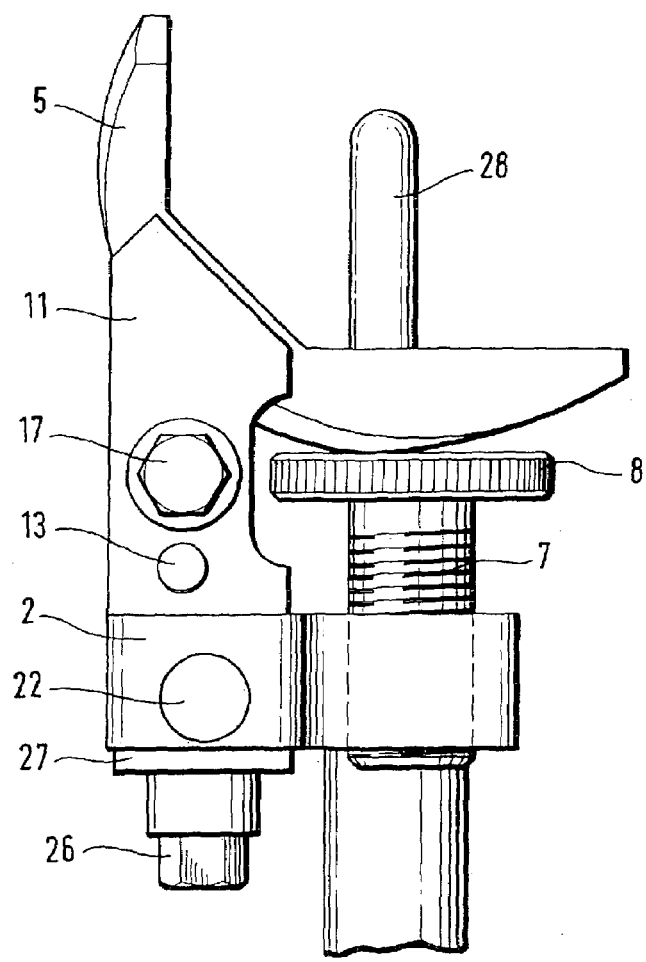
FIG. 4 shows a side view of the front part of the instrument.
Figure 5:
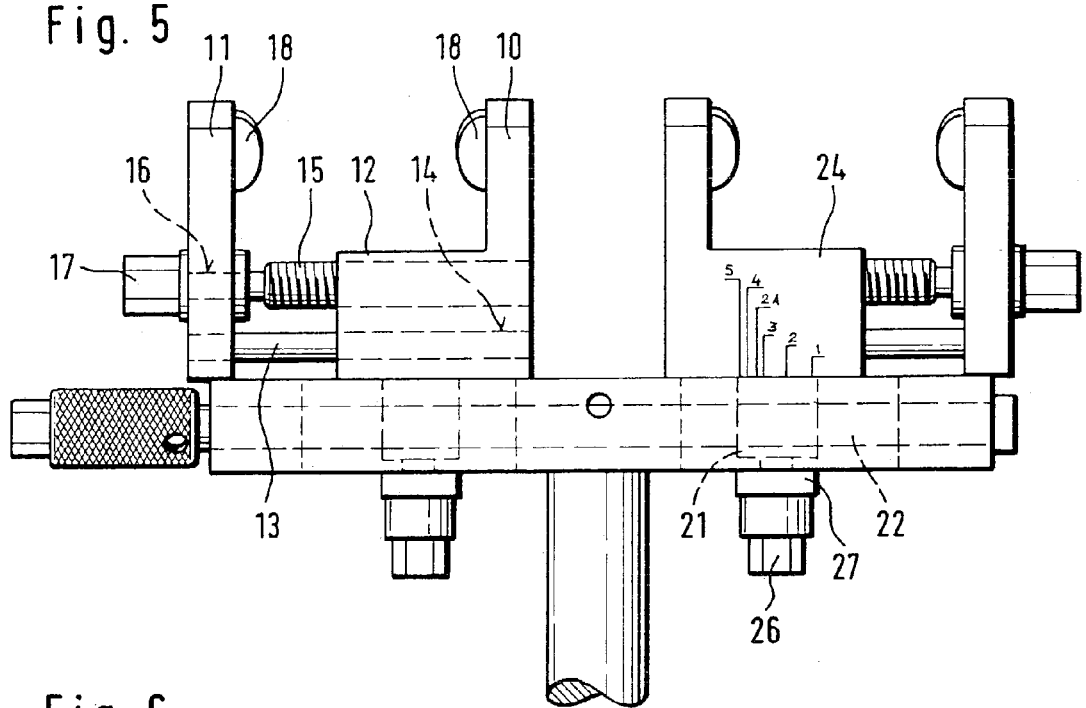
FIG. 5 shows a rear view of the front part of the instrument.
Figure 6:
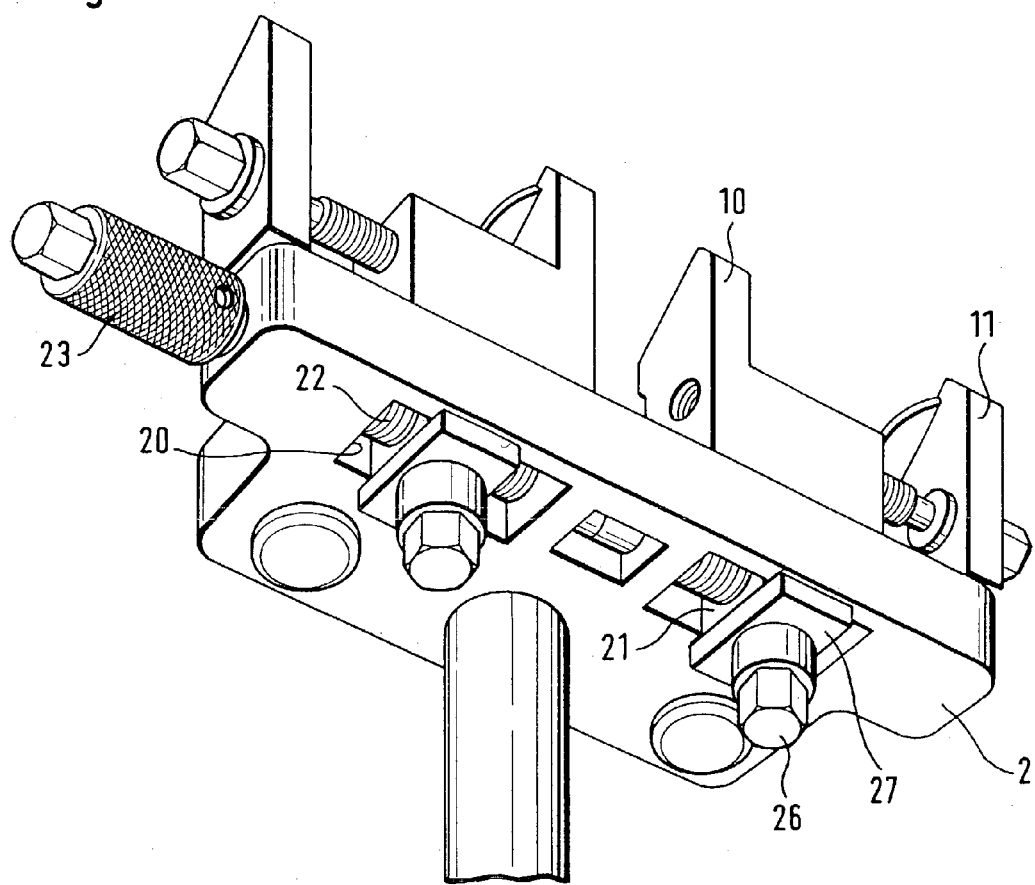
FIG. 6 shows a view of the front part of the instrument obliquely from behind.

The slide-surface supports 6 consist of a threaded shaft 7, mounted in the supporting plate, and of a head 8 which contains an impact cushion 9 of rigidly elastic plastic, for example polyethylene. The surface of the head 8 is substantially plane. By turning the slide-surface support by way of a knurled edge provided on the head 8, it can be adjusted so that its top face bears with a supporting action on the slide surface of the prosthesis part located in the associated clamp 4, as is shown in FIG. 4.

Each clamp 4 comprises a first clamping jaw 10 and a second clamping jaw 11. The foot 12 of the first clamping jaw 10 is held by the holding plate 2 in a manner which will be explained later. The second clamping jaw 11 is held by the foot 12 of the first clamping jaw 10 so as to be displaceable in parallel thereto. For this purpose, a guide rod 13 is arranged rigidly on the second clamping jaw 11 and is guided in a bore 14 of the foot 12. A threaded spindle 15 is also provided which can be screwed in the foot 12 and whose end is mounted in a bore 16 of the second clamping jaw. By turning the head 17 of the spindle 15, the spacing of the clamping jaws 10, 11 can thus be adjusted.

Both clamping jaws 10, 11 carry elongate projections 18 lying opposite one another. The sliding prostheses 5 comprise, at a corresponding position, matching slits into which the projections 18 engage when the prostheses are inserted into the clamps. In this way, the prostheses are positioned relative to the instrument.

The supporting plate 2 comprises, under each of the feet 12, a guide slit 20 which extends in the transverse direction of the instrument (parallel to the guide rod 13) and in which a matching slide block 21 is guided which is connected rigidly to the foot 12. A continuous spindle 22 lies lengthwise in the two guide slits 20. It is mounted rotatably but axially immovably in the supporting plate 2 and can be rotated by means of a knurled head 23. It has a threaded portion in the area of each of the two slits 20. The threaded portions lie in matching threaded bores of the slide blocks 21 and have opposite threads. If the head 23 of the spindle is rotated, the clamps 4 are moved toward one another or moved away from one another depending on the direction of rotation. Their spacing, and thus the spacing of the sliding prostheses held by them, can in this way be adjusted in the manner desired. To make the adjustment easier, a scale 24 is used which interacts with a corresponding marking on the supporting plate.

On the underside of the supporting plate 2, the slide blocks 21 are connected to transverse yokes 27 via binding screws 26. These can be tightened in the desired setting of the clamps in order to fix the position of the clamps. If they are tightened only slightly, the clamps 4 remain displaceable on the supporting plate 2, but their play relative to the supporting plate can be adjusted. The instrument is used in the following way. After choosing the suitable size of the sliding prostheses 5, the latter are inserted into the clamps 4 of the instrument, and the slide-surface supports 6 are adjusted so that they bear with a supporting action on the slide surfaces of the prostheses. According to the anatomical conditions, or according to the measurements of a tibial prosthesis possibly to be used in conjunction with the sliding prostheses, the spacing of the sliding prostheses from one another is adjusted by means of the spindle 22. The prostheses are then implanted in the known manner. For the force transmission which is to be applied, it is helpful that the grip 1 is substantially flush with the slide-surface supports 6 and the anchoring pins 28 of the prostheses 5 (see FIG. 4). For the force transmission to the prostheses, and for securing their position, it is also advantageous that the slide-surface supports 6 and the projections 18 provided on the clamps 4 have a relatively substantial distance 29 from one another in the anterior-posterior direction, the reason being that the slide-surface supports 6 act on that part of the slide surfaces which extends in the anterior-posterior direction, whereas the projections 18 interact with a portion of the prostheses whose slide surface is on average inclined by at least 30° (45° in the example shown) relative to the anterior-posterior direction.

After the prostheses have been attached to the femur, the clamps 4 are opened so far that the spacing between the projections 18 is greater than the width of the prostheses. Since the projections located on the first clamping jaws 10 thereafter still engage in the associated grooves of the prostheses, the clamps are moved toward one another by actuating the spindle head 23 until the instrument can be removed from the prostheses.

The invention claimed is:

1. An insertion instrument for a pair of sliding prostheses, comprising:

a supporting plate;

two clamps separated by a distance that is adjustable through a spacing range, each of which clamps is configured to receive one of the pair of sliding prostheses and has clamping jaws configured to interact with side edges of the corresponding sliding prostheses; and two vertically adjustable sliding-surface bearing supports mounted offset from the clamps in horizontally fixed positions on the supporting plate and configured to support the sliding prostheses in the area of the sliding surfaces thereon, the supporting plate comprising a slide guide formed thereon and an adjustment spindle for at least one of the two clamps and the sliding-surface bearing supports having a distance therebetween which corresponds to the adjustable spacing range of the clamps.

2. The instrument as claimed in claim 1, wherein only one adjustment spindle with opposite threads is provided for both clamps.

3. The insertion instrument as claimed in claim 1 or 2, wherein one of the clamping jaws of at least one of the clamps is connected directly to the supporting plate and the other of the clamping jaws of the at least one clamp is adjustable relative thereto.

4. The insertion instrument as claimed in claim 3, wherein the slide surfaces extend in an anterior-posterior direction.

5. The insertion instrument as claimed in claim 3, wherein the insertion instrument is configured to engage anchoring pins on the sliding prostheses that act in a direction corresponding to the direction of the sliding surfaces.

6. The insertion instrument as claimed in claim 2 or 1, wherein the-slide surfaces extend in an anterior-posterior direction.

7. The insertion instrument as claimed in claim 6, wherein the insertion instrument is configured to engage anchoring pins on the sliding prostheses that act in a direction corresponding to the direction of the sliding surfaces.

8. The insertion instrument as claimed in claim 2 or 1, wherein the insertion instrument is configured to engage anchoring pins on the sliding prostheses that act in a direction corresponding to the direction of the sliding surfaces.

* * * * *